United States Patent [19]

Takita et al.

[11] 4,382,955

[45] May 10, 1983

[54] DERIVATIVE OF 4-(N-(3,4-DIHYDROXYBENZYLIDENE) AMINOMETHYL CYCLOHEXANE-1-CARBOXYLIC ACID

[75] Inventors: Hitoshi Takita; Yutaka Mukaida; Sakuo Noda; Hidetoshi Kobayashi, all of Tokyo, Japan

[73] Assignee: Kureha Kagaku Kogyo Kabushiki Kaisha, Tokyo, Japan

[21] Appl. No.: 267,250

[22] Filed: May 26, 1981

[30] Foreign Application Priority Data

Jun. 4, 1980 [JP] Japan ................................. 55-75055
Feb. 24, 1981 [JP] Japan ................................. 56-25990

[51] Int. Cl.³ .................... C07C 61/08; A61K 31/215
[52] U.S. Cl. .................................... 424/309; 560/35; 562/440; 424/319
[58] Field of Search ................. 560/35; 562/440; 424/309, 319

[56] References Cited

U.S. PATENT DOCUMENTS 2,577,900 12/1951 Lisk et al. ............................ 560/35
3,697,589 10/1972 Menasse et al. ..................... 560/35
4,198,349 4/1980 Ness, Jr. et al. .................... 560/35

FOREIGN PATENT DOCUMENTS 55-145652 11/1980 Japan ................................. 424/309
174617 9/1965 U.S.S.R. ............................ 562/440

OTHER PUBLICATIONS

Wagner et al., Synthetic Organic Chemistry, John Wiley & Sons, Inc., NY., pp. 728–729 (1965).
Gera et al., Chem. Absts., 91, 157328(q), 1979.

*Primary Examiner*—Bernard Helfin
*Attorney, Agent, or Firm*—Wegner & Bretschneider

[57] ABSTRACT

A novel compound of 4-[N-(3',4'-dihydroxybenzylidene) aminomethyl]cyclohexane-1-carboxylic acid or a salt or an ester thereof which has specific pharmacologic activities, a method for preparing thereof and a pharmaceutical composition comprising thereof as an active ingredient are provided.

6 Claims, 6 Drawing Figures

DERIVATIVE OF 4-(N-(3,4-DIHYDROXYBENZYLIDENE) AMINOMETHYL CYCLOHEXANE-1-CARBOXYLIC ACID

This invention relates to a novel derivative of 4-[N-(3',4'-dihydroxybenzylidene)aminomethyl]cyclohexane-1-carboxylic acid and a pharmaceutical composition comprising thereof.

It is an object of the invention to provide a novel compound of 4-[N-[3',4'-dihydroxybenzylidene)aminomethyl]cyclohexane-1-carboxylic acid or a salt or an ester thereof. An another object of the invention is to provide a method for preparing the novel compound. Furthermore, still another object is to provide a pharmaceutical composition comprising a pharmaceutically effective amount of the novel compound as an active ingredient.

The novel compound of 4-[N-(3',4'-dihydroxybenzylidene)aminomethyl]cyclohexane-1-carboxylic acid (hereinafter referred to as the compound of the invention) is represented by the formula (I):

wherein the cyclohexane ring includes trans- and cis form.

The compound of the invention includes salts or esters of 4-[N-(3',4'-dihydroxybenzylidene)aminomethyl]cyclohexane-1-carboxylic acid. The salt is an alkali or alkaline earth metal salt such as sodium salt, potassium salt, calcium salt, magnesium salt, etc., or substituted- or non-substituted ammonium salt. The ester is a lower alkyl ester of which an alkyl group has 1 to 3 carbon atoms, such as methyl-, ethyl- or n- or isopropyl group.

The compound of the invention is preferably prepared by the method described below, although it may be prepared by the conventional method. Namely, 3,4-dihydroxybenzaldehyde represented by the formula (II):

is brought into reaction with 4-aminomethyl-cyclohexane-1-carboxylic acid represented by the formula (III):

wherein the cyclohexane ring includes trans- and cis form, or a lower alkyl ester thereof, and the compound of the invention (acid- or ester form) is obtained by dehydrating-condensation.

The reaction of the compound of the formula (II) with the compound of the formula (III) or an ester thereof is carried out in an organic solvent at lower than 150° C., preferably 0° to 120° C., under atmospheric inert gas. At higher than 150° C., the yield of the desired product is reduced because of various side reactions. Any organic solvent may be used for the reaction if it does not participate in the reaction. A lower alcohol such as methanol or ethanol, benzene, toluene, dimethylformamide, acetonitrile or the like is conventionally used for the solvent.

Since the reaction takes place together with dehydrating, the reaction is carried out in the presence of a dehydrating agent or while removing water formed by the reaction under the reflux of the solvent. An anhydride of a lower alcohol such as an anhydrous methanol or ethanol can be used for the solvent and at the same time for the dehydrating agent.

The compound of the invention is isolated by treating the reaction mixture with a known method after the reaction.

The compound of the invention of salt formed is prepared by the conventional method for neutralization by using a base such as hydroxide, carbonate or bicarbonate of an alkali or alkaline earth metal for example sodium, potassium, calcium or magnesium, ammonia or primary-, secondary- or tertiary amine. For example, a sodium salt is obtained by neutralizing the compound of the invention (an acid form) obtained by the above-mentioned reaction with an alcoholic- or aqueous solution of sodium hydroxide under atmospheric inert gas at lower than 100° C., usually at 0° to 50° C.

The method mentioned above is only an embodiment of the method for preparing the compound of the invention, and the method of the invention is not restricted to the method as above.

The compound of the invention shows an inhibitory effect on platelet aggregation, polynuclear leukocyte migration, exudation of polynuclear leukocytes into the inflammatory site and proliferation of inflammatory granuloma, an prophylactic effect on the adjuvant arthritis, an antineoplastic effect in animals, a low acute toxicity, no lesion on the gastric mucosa and no mutagenicity, as will be shown in Examples. Accordingly, the compound of the invention is useful as a remedy for various diseases such as inflammation, thrombosis, encephalorrhagia, hypertension, asthma or cancer in animals, etc., especially for chronic diseases such as rheumatism or systemic lupus erythematosus (SLE), etc.

When the compound of the invention is used for a pharmaceuticals, the salt or the ester must be pharmaceutically acceptable.

Furthermore, the compound of the invention may be used as an active ingredient of a pharmaceutical composition for the above-mentioned diseases.

The compound of the invention can be administered perorally, rectally or through injection in the various dosage forms as a composition together with a pharmaceutically acceptable carrier and/or an adjuvant. In these cases, a mixture of two or more kinds of the compound of the invention or a mixture together with other pharmaceutically active materials may be used as an active ingredient of a pharmaceutical composition.

The dosage form of the composition may be tablet, sublingual tablet, powder, capsule, troch, aqueous or oily solution, suspension, emulsion, syrup, aqueous or oily injection. An example of the carrier mentioned above is water, gelatin, lactose, starch, pectin, magnesium stearate, stearic acid, talc, vegetable oil, gum arabic, polyalkylene glycol, vaseline, sorbitan trioleate, polyoxyethylene-sorbitan monooleate, alkylphenol, aliphatic alcohol, polyvinylpyrrolidone, or the like. In the composition, if necessary, edulcorant, flavor, tinctorial agent, preservative, salt for osmoregulation or buffer, that is, the conventional pharmaceutical adjuvant may be used together.

The content of the compound of the invention in the pharmaceutical composition may be adequately varied, however, it is 0.01%–100% by weight, preferably 0.05%–80% by weight of the composition.

The pharmaceutical composition of the invention is administered to a human or animal parenterally, for example, rectally, through injection (hypodermic, intramuscular or intravenous, or drip), preferably perorally (for example sublingual etc.).

A dose of the pharmaceutical composition of the invention is 0.1 to 500 mg, preferably 0.5 to 200 mg per day per one kilogram of the body weight in the case of peroral administration to a human, and 0.01 to 200 mg, preferably 0.1 to 100 mg in the case of parenteral administration, and the pharmaceuticals is administered one to four times a day. However the dose of the pharmaceutical composition depends on age, individuality, condition of a disease etc. of a human or animal, and the dose out of the above-mentioned range may be used.

The properties, method for preparation and pharmacologic effects of the compound of the invention are concretely described while referring to the examples.

EXAMPLE 1

Preparation of trans-4-[N-(3',4'-dihydroxybenzylidene)aminomethyl]-cyclohexane-1-carboxylic acid Into 30 ml of dehydrated and purified methanol, 1.753 g (12.7 m mol) of 3,4-dihydroxybenzaldehyde was dissolved. The resulting solution was dropped into 1.994 g (12.7 m mol) of trans-4-aminomethyl-cyclohexane-1-carboxylic acid under atmospheric nitrogen, and the mixed solution was refluxed for 3 hours while stirring. After cooling the reaction mixture to room temperature, the deposited orange-yellow crystal was filtered, washed with methanol and vacuum-dried. 2.9 g of trans-4-[N-(3',4'-dihydroxybenzylidene)aminomethyl]cyclohexane-1-carboxylic acid was obtained with the yield of 82.7%.

The characteristics of the compound of the invention (acid form) thus obtained were as follows:

(1) melting point; 222° C. with decomposition, (measured by the Capillary Method)

(2) elementary analysis;

|  | C (%) | H (%) | N (%) |
|---|---|---|---|
| theoretical: | 64.97 | 6.91 | 5.05 |
| experimental: | 64.6 | 7.1 | 5.0 |

Figure 1:
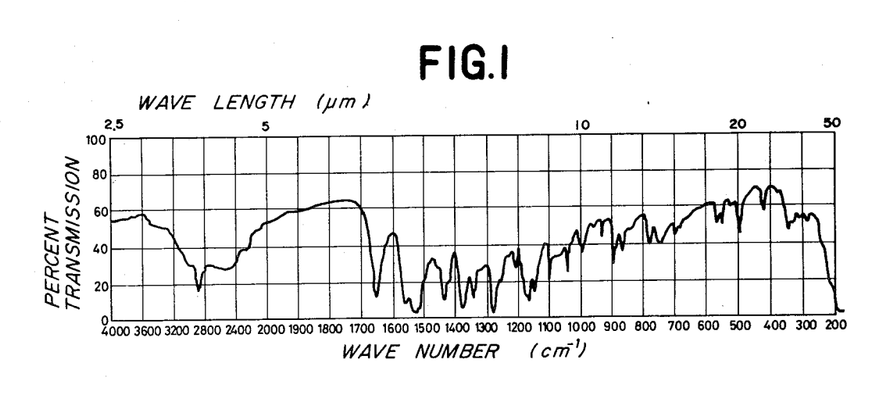

(3) nuclear magnetic resonance (NMR) spectrum in dimethyl sulfoxide;

δ=0.9–2.0 (9H, m), 2.1–2.2 (1H), 3.33 (2H, d), 6.73 (1H, d), 6.97 (1H, d), 7.19 (1H, s), 8.03 (1H, s), (4) infrared absorption (IR) spectrum by KBr tablet method; shown in FIG. 1.

EXAMPLE 2

Preparation of sodium trans-4-[N-(3',4'-dihydroxybenzylidene)aminomethyl]-cyclohexane-1-carboxylate Into 3.6 ml of 1 N methanolic solution of sodium hydroxide, 1.00 g (3.61 m mol) of trans-4-[N-(3',4'-dihydroxybenzylidene)aminomethyl]cyclohexane-1-carboxylic acid obtained in Example 1 was added, and dissolved while stirring for 20 to 30 min at room temperature under atmospheric nitrogen. After filtration, methanol was evaporated off and 1.121 g of sodium trans-4-[N-(3',4'-dihydroxybenzylidene)aminomethyl]-cyclohexane-1-carboxylate was obtained.

Figure 2:
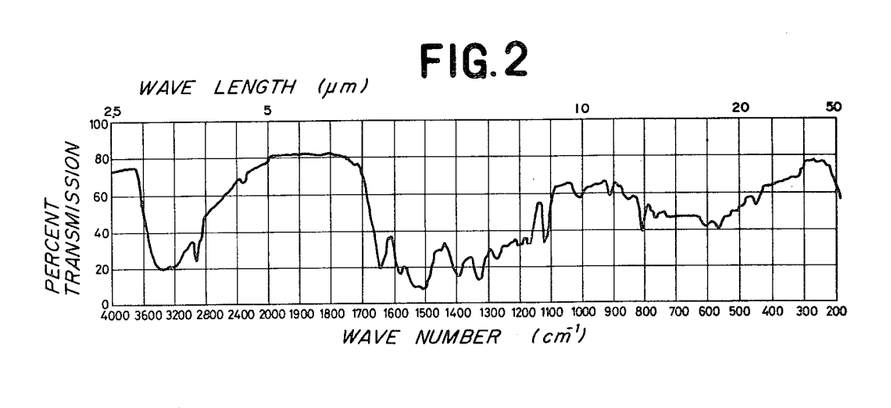

IR spectrum (KBr tablet method) of the compound of the invention (sodium salt) thus obtained is shown in FIG. 2. In ultraviolet (UV) absorption spectrum in methanol the following two maxima were observed:

λmax: 271.5 mμ and 309 mμ.

EXAMPLE 3

Preparation of ethyl trans-4-[N-(3',4'-dihydroxybenzylidene)aminomethyl]-cyclohexane-1-carboxylate Into 20 ml of methanol, 0.835 g of 3,4-dihydroxybenzaldehyde and 1.2 g of ethyl trans-4-aminomethyl-cyclohexane-1-carboxylate were dissolved. The resulting solution was refluxed to react for one hour under atmospheric nitrogen. After leaving the reaction mixture at 0° C. for a night, the deposited purple plate-crystal was filtered and dried to obtain 1.525 g of the compound of the invention (ethyl ester).

The characteristics of the ethyl ester thus obtained were as follows:

(1) melting point; 50°–62° C., (measured by the Capillary Method)

(2) elementary analysis;

|  | C (%) | H (%) | N (%) |
|---|---|---|---|
| theoretical: | 66.86 | 7.59 | 4.59 |
| experimental: | 66.2 | 7.7 | 4.3 |

Figure 3:
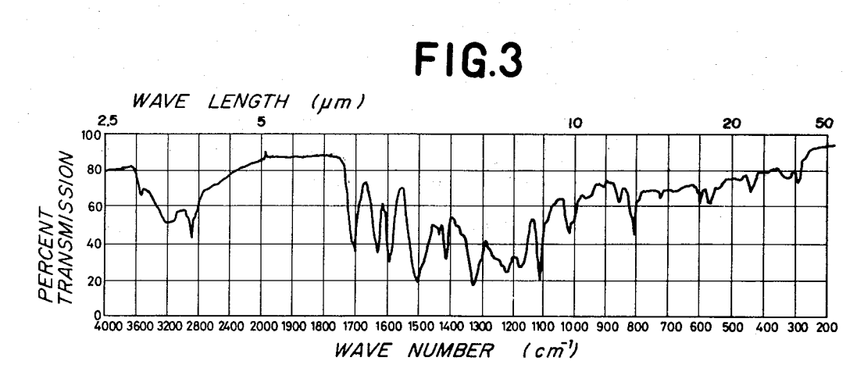

(3) IR spectrum; shown in FIG. 3.

EXAMPLE 4

Preparation of cis-4-[N-(3',4'-dihydroxybenzylidene)aminomethyl]cyclohexane-1-carboxylic acid In dehydrated and purified methanol, 0.395 g (2.86 m mol) of 3,4-dihydroxybenzaldehyde was refluxed to react with 0.450 g (2.86 m mol) of cis-4-aminomethyl-cyclohexane-1-carboxylic acid for one hour. After evaporating methanol off under a reduced pressure from the uniform red-orange reaction mixture, 0.7910 g of yellow powder of cis-4-[N-(3',4'-dihydroxybenzylidene)aminomethyl]cyclohexane-1-carboxylic acid was obtained.

The characteristics of the compound of the invention (cis form) thus obtained were as follows:

(1) melting point; 121°–129° C., (measured by the Hot-Plate Method)

(2) NMR in dimethylsulfoxide;

δ=1.02–1.84 (9H, m), 2.0–2.1 (1H), 3.35 (2H, d), 6.82 (1H, d), 6.97 (1H, d), 7.20 (1H, s), 8.04 (1H, s).

EXAMPLE 5

Inhibitory effect on platelet aggregation and polynuclear leukocyte migration, and acute toxicity Pharmacologic activities and acute toxicity of the compound of the invention were examined. Specimens examined are as follows:

Specimen I;
  Sodium trans-4-[N-(3',4'-dihydroxybenzylidene)aminomethyl]cyclohexane-1-carboxylate obtained in Example 2,
  II; Sodium salt of cis-4-[N-(3',4'-dihydroxybenzylidene)aminomethyl]cyclohexane-1-carboxylic acid obtained in Example 4, Comparative Specimen
  III; indomethacin,
  IV; homochlorcyclizine.

Comparative Specimens III and IV having the similar pharmacologic activities as the compound of the invention are commercially available in Japan.

The examination was carried out according to the methods described below.

(1) Examination method for inhibitory effect on platelet aggregation

Rabbit platelet rich plasma (PRP) was used for Aggregation Tests. PRP was prepared by centrifugation of blood collected from the ear vein of Rabbit and diluted into number-concentration 300,000/μl with platelet poor plasma. Platelet aggregation was induced by Sodium Arachidonate and monitored (measured) with a four channel platelet aggregation Tracer RAT-4A (Niko Bioscience Co., Japan). Aggregation Tracer tube containing 230 μl PRP was preincubated at 37° C. for 5 min with each Specimen.

(2) Examination method for inhibitory effect on polynuclear leukocyte migration Rat's polynuclear leukocyte migration was examined by Boyden method (refer to Japanese J. Clin. Med., 27(9), 172 (1969)) as follows; a mixture of 10 parts by volume of culture filtrate of *E. coli* and one part by volume of serum was incubated at 37° C. for one hour and diluted into 5-times by volume with physiological salt solution, and the resulting mixture was used as an attractant. After preincubating polynuclear leukocyte suspension with each specimen for 10 min, migration of polynuclear leukocytes was examined.

(3) Examination method for acute toxicity

Acute toxicity was examined by administering perorally an aqueous solution of each Specimen to female JCL-ICR mouse of 5 to 6 weeks after birth.

The results are shown in Table 1.

TABLE 1

| Specimen | Platelet aggregation $ID_{100}(\mu M)^{(1)}$ | Inhibition rate of polymorphonuclear leukocyte migration (%)$^{(2)}$ | | | | Acute toxicity $LD_{50}(mg/kg)^{(3)}$ |
|---|---|---|---|---|---|---|
| | | 1 μM | 10 μM | 100 μM | 1000 μM | |
| I | 13–20 | 15 | 44 | 81 | 100 | >3000$^{(4)}$ |
| II | 120 | | | 45.9 | | >3000 |
| III | 0.5–1 | 0 | 0 | 25 | 79 | 30 |
| IV | ≧1000 | 15 | 48 | 80 | 100 | 350 |

Notes:
$^{(1)}$The minimum concentration (μM) of each Specimen for inhibiting completely (100%) the platelet aggregating effect of sodium arachidonate (tested at 400 μM).
$^{(2)}$The average value of inhibition rate (%) of polynuclear leukocyte migration at each concentration (μM) of each Specimen.
$^{(3)}$Median lethal dose ($LD_{50}$), that is, dose for getting 50% of mice to death, in unit of mg per one kilogram of body weight of mouse.

As shown in Table 1, the compound of the invention has inhibitory effects on platelet aggregation and polynuclear leukocyte migration, and a low acute toxicity. Accordingly, the compound of the invention can be used as an anti-inflammatory and a remedy for other various diseases.

EXAMPLE 6

Inhibitory effect on polynuclear leukocyte exudation

Inhibitory effect of sodium trans-4-[N-(3',4'-dihydroxybenzylidene)aminomethyl]cyclohexane-1-carboxylate on exudation of polynuclear leukocytes into inflammatory site was examined by using male rats (Donryu) of body weight of about 150 g of Granuloma CMC pouch method (refer to Yakugaku Zasshi, 88, 1472, (1968)).

After shearing the rat on the dorsum about 5 cm in diameter, 5 ml of air was hypodermically injected into the site to form a pouch. After 24 hours, 5 ml of aqueous 2% (W/V) solution of CMC sodium salt at 37° C. was injected into the pouch, and at the same time an aqueous solution of the compound of the invention was administered perorally to the rat at a dose of 50, 100 and 200 mg/kg. For comparison, indomethacin was administered perorally to the rat at a dose of 10 mg/kg in the form of an aqueous suspension.

Figure 4:
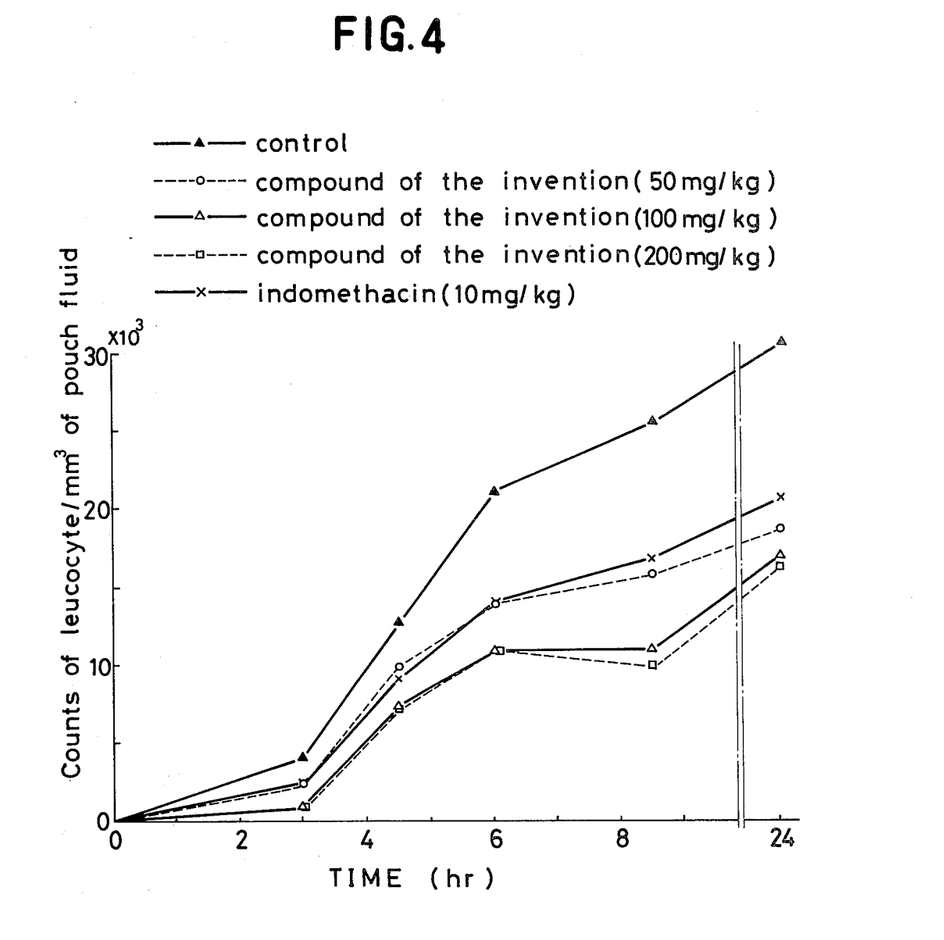

After the injection of CMC, the liquid in the pouch was collected as the time passed by in an amount of 0.5 ml and stained. Then the number of polynuclear leukocytes exudated into the pouch was counted. The results is shown in FIG. 4. As shown in FIG. 4, the compound of the invention can adjust the exudation of polynuclear leukocytes while depending on its dose.

In addition, ethyl trans-4-[N-(3',4'-dihydroxybenzylidene)aminomethyl]cyclohexane-1-carboxylate was examined in the same manner, and the ester also inhibited the exudation of polynuclear leukocytes.

EXAMPLE 7

Inhibitory effect on proliferation of inflammatory granuloma

Inhibitory effect of sodium trans-4-[N-(3',4'-dihydroxybenzylidene)aminomethyl]cyclohexane-1-carboxylate on proliferation of inflammatory granuloma was examined by using male rate (Donryu) of 5 weeks after birth and the method of Fujimura et al. (refer to Pharmacometrics, 19 (3), 329 (1980)).

A sheet of filter paper of 13 mm in diameter and 0.26 mm in thickness was immersed into an aqueous 2% solution of CMC containing 0.1 mg/ml of dihydroxystreptomycin and penicillin (million units). Thus treated sheet was inserted hypodermically on the dorsum of the etherized rat. After palinesthesia, the compound of the invention was administered perorally once a day for 8 days at a dose of 25, 50 and 100 mg/kg/day, and for comparison, indomethacin was administered in the same manner at a dose of 3 mg/kg/day. The body weight gain, the weight of granuloma and the lesion on gastric mucosa were examined on the nineth day.

The results are shown in Table 2.

TABLE 2

| Pharma-ceutics | Dose mg/kg/day | Number of rats used | Granuloma Dry weight (mg) | Inhibitory rate (%) | Body weight gain (%) | Lesion on stomachal mucous membrane |
|---|---|---|---|---|---|---|
| Control[1] | 0 | 4 | 330.2 ± 73.9 | — | 29 | none |
| Compound of the invention | 25 | 4 | 155.6 ± 13.8 | 52.9[2] | 28 | none |
|  | 50 | 4 | 118.8 ± 46.0 | 64.0[2] | 32 | none |
|  | 100 | 5 | 73.6 ± 31.3 | 77.7[2] | 37 | none |
| Indomethacin | 3 | 5 | 160.5 ± 73.1 | 51.4[3] | 23 | petechiae[4] |

Notes:
[1]The compound of the invention is not administered,
[2]$p < 0.01$, P denotes the limit of statistical confidence,
[3]$p < 0.05$,
[4]Petechiae were observed in two rats.

As shown in Table 2, the compound of the invention inhibits effectively the proliferation of inflammatory granuloma while depending on the dose administered, and does not inhibit the weight gain by administration. Furthermore, no side effects such as the lesion on the stomachal mucous membrane seen in using the conventional non-steroidal anti-inflammatory were observed.

EXAMPLE 8

Lesion on gastric mucosa

The conventional anti-inflammatories may often cause the lesion on the gastric mucosa as a side-effect. The possibility of the compound of the invention in causing such a lesion was examined by using the method of Fujimura et al. as in Example 7.

After fast of female JCL-SD rat for 24 hours, sodium trans-4-[N-(3',4'-dihydroxybenzylidene)aminomethyl]-cyclohexane-1-carboxylate was administered perorally to the rat. After 3 hours, the rat was slaughtered. Then the stomach was enucleated, and the length (mm) of the lesion on the gastric mucosa was measured by the method of Okabe et al. (refer to Pharmacometrics, 18 (1), 1 (1979)). The total sum of the length was used as the Ulcer Index. For comparison, indomethacin was administered perorally at a dose of 30 mg/kg. The results are shown in Table 3.

TABLE 3

| Pharmaceutics | Dose (mg/kg) | Number of rats | Ulcer Index |
|---|---|---|---|
| Control[1] | 0 | 2 | 0 |
| Compound of the invention[2] | 200 | 2 | 0 |
|  | 500 | 3 | 0 |
| Indomethacin[3] | 30 | 3 | 30.5 |

Notes:
[1]The compound of the invention is not administered.
[2]Administered perorally in the form of an aqueous solution.
[3]Administered perorally in the form of an aqueous suspension.

As shown in Table 3, the compound of the invention, even at a high dose as 500 mg/kg, did not cause the lesion on the stomachal mucous membrane.

EXAMPLE 9

Prophylactic effect on adjuvant arthritis

Prophylactic effect of the compound of the invention on adjuvant arthritis was examined by using 6 female JCL-SD rats of 7 weeks after birth as one group and the conventional method (refer to Fujihira et al., Pharmacometrics, 5(2), 169–183, (1971)).

Freund's complete adjuvant (0.6 mg/0.1 ml) was inoculated into the right hind paw of the etherized rat. After palinesthesia, the sodium trans-4-[N-(3',4'-dihydroxybenzylidene)aminomethyl]cyclohexane-1-carboxylate was administered perorally once a day for 24 continuous days. The change of hind paw volume and body weight due to adjuvant arthritis was examined as the time passed by. For comparison, a steroid (prednisolone) was administered perorally in the same manner.

Figure 5:
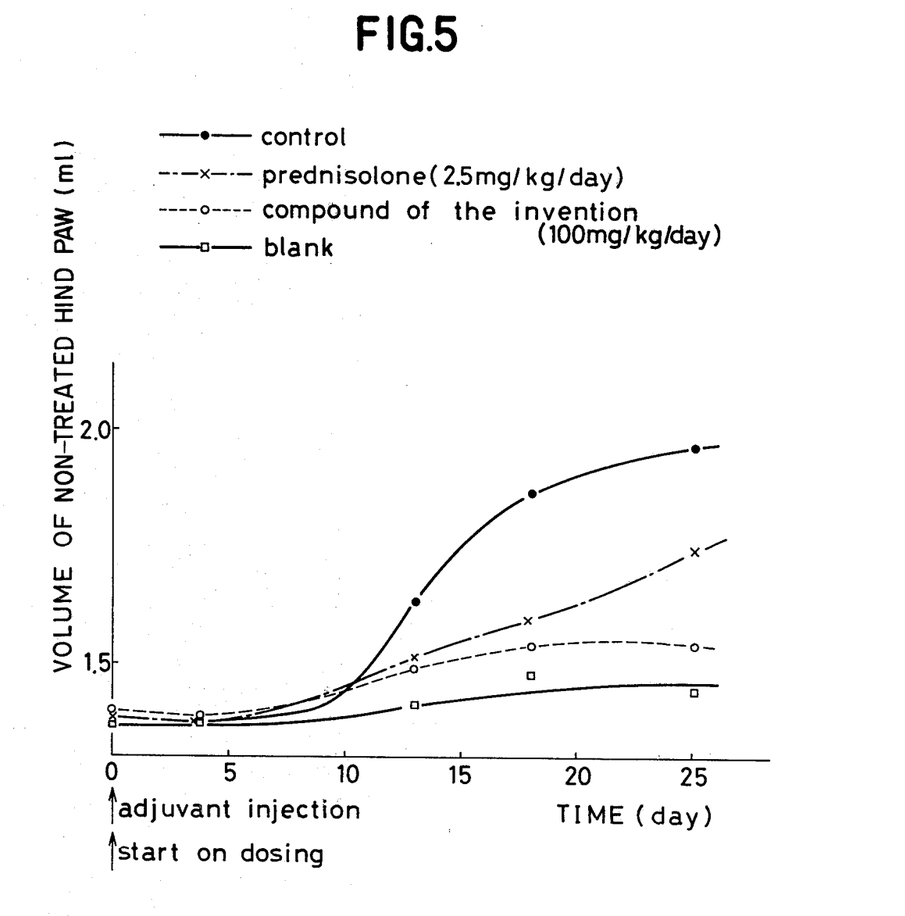
Figure 6:
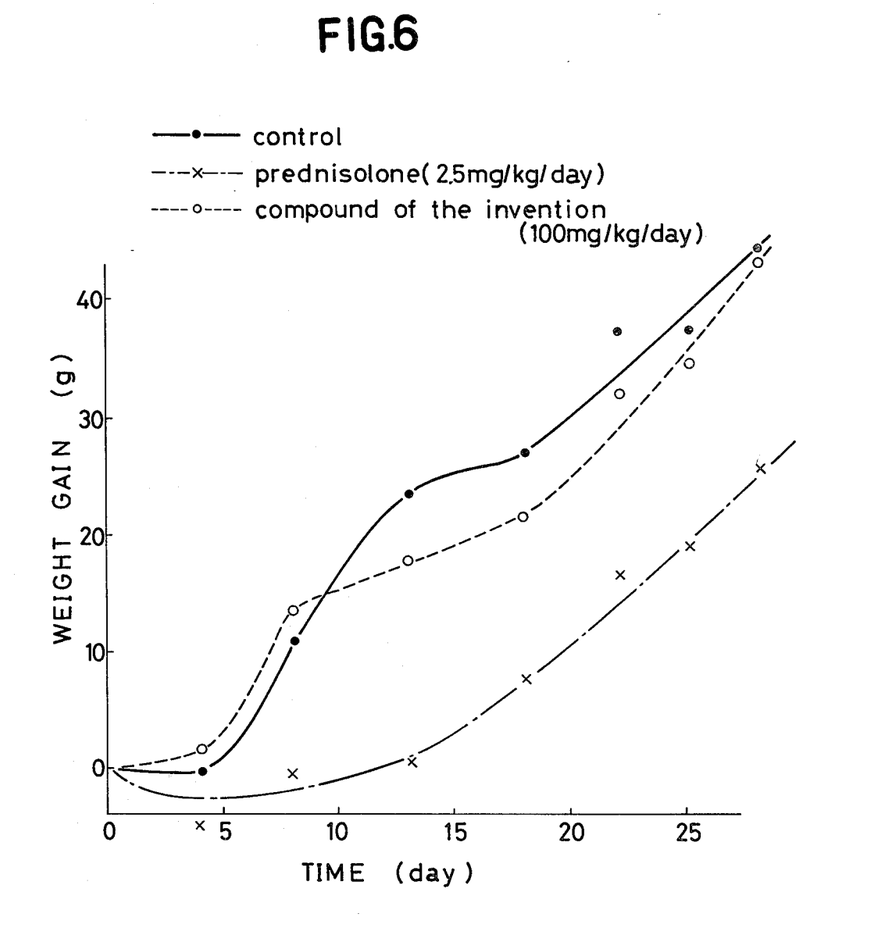

The results are shown in FIGS. 5 and 6. In FIG. 5, "blank" denotes no inoculation of the adjuvant. As shown in FIGS. 5 and 6, the compound of the invention prevented effectively the adjuvant arthritic without any body weight reduction of the rat which is often seen in the rat administered with a steroid.

In addition, the rat was slaughtered at 25th day from the inoculation of the adjuvant and the weight of each organ of the rat was measured. No involution of thymus was observed in the rats administered with the compound of the invention, while significant involution of thymus was observed in the rats administered with the steroid (prednisolone). Accordingly, the compound of the invention is usable as a remedy for chronic diseases such as rheumatism.

EXAMPLE 10

Antineoplastic effect

Antineoplastic effect of the compound of the invention was examined.

Into the infra-axillary site of ICR-JCL mouse, $1 \times 10^6$ cells of Sarcoma-180 was implanted. After 24 hours of implantation, the solution of sodium trans-4-[N-(3',4'-dihydroxybenzylidene)aminomethyl]cyclohexane-1-carboxylate dissolved into the sterilized and purified water for injection was administered perorally once a day for continuous 21 days at a dose of 100 and 500 mg/kg. On 22nd day after implantation, neoplastic tuberculum was enucleated, and the inhibition rate (I.R. in %) was calculated according to the following formula:

$$(1 - T/e) \times 100 = I.R. \ (\%)$$

wherein T and e denotes the mean weights of neoplasm of the administered and control groups, respectively.

I.R. values were 55.8 and 45.3% at a dose of 100 and 500 mg of the compound of the invention, respectively.

EXAMPLE 11

Mutagenicity

Mutagenicity of the compound of the invention was examined by Rec-assay.

Bacillus subtilis M 45 (a strain deficient in recombinational repair) and B. subtilis H 17 (a strain retaining recombinational repair) were streaked onto B-II agar culture so that the start points of the two streaks did not overlapped together. The B-II agar culture was prepared by dissolving 10 g of meat extract, 10 g of polypeptone, 5 g of sodium chloride and 15 g of agar into 1000 ml of distilled water and adjusting pH to 7.0.

As soon as a solution of sodium trans-4-[N-(3',4'-dihydroxybenzylidene)aminomethyl]cyclohexane-1-carboxylate was absorbed into a circular filter paper (disk) of 8 mm in diameter, the start points of the two streaks were covered with the filter paper. After incubating the strains at 37° C. for a night, the length of growth inhibition zone was measured. Kanamycin as a negative control and mitomycin as a positive control were used. The results are shown in Table 4.

TABLE 4

| Pharmaceutics | Concentration (μg/disk) | Growth inhibition Zone (mm) | | |
|---|---|---|---|---|
| | | M45 | H17 | Difference |
| Compound of the invention | 100 | 0 | 0 | 0 |
| | 500 | 0 | 0 | 0 |
| | 1,000 | 0 | 0 | 0 |
| | 5,000 | 3 | 3 | 0 |
| Kanamycin | 10 | 6 | 5 | 1 |
| | 100 | 10 | 10 | 0 |
| Mitomycin | 0.05 | 4 | 0 | 4 |
| | 0.50 | 15 | 9 | 6 |

As shown in Table 4, the compound of the invention showed no mutagenicity, and has been found to have high safety.

From the results of Examples 5 to 11, the compound of the invention has been found to show very specific pharmacologic activities, no toxicity and no side-effect. Accordingly the compound of the invention can be used for a pharmaceutical composition which has high safety and is a remedy or a protectant for various diseases.

What is claimed is:

1. A compound of 4-[N-(3',4'-dihydroxybenzylidene)aminomethyl]cyclohexane-1-carboxylic acid or a salt or an ester thereof.

2. The compound of claim 1, which is trans-4-[N-(3',4'-dihydroxybenzylidene)aminomethyl]cyclohexane-1-carboxylic acid.

3. The compound of claim 1, which is sodium trans-4-[N'-(3',4'-dihydroxybenzylidene)aminomethyl]cyclohexane-1-carboxylate.

4. The compound of claim 1, which is ethyl trans-4-[N-(3',4'-dihydroxybenzylidene)aminomethyl]cyclohexane-1-carboxylate.

5. The compound of claim 1, which is cis-4-[N-(3',4'-dihydroxybenzylidene)aminomethyl]cyclohexane-1-carboxylic acid.

6. A pharmaceutical composition in dosage unit form, having an inhibitory function on platelet aggregation and polynuclear leukocyte migration, comprising an effective amount of 4-N-(3',4'-dihydroxybenzylidene)aminomethyl cyclohexane-1-carboxylic acid or esters thereof or a pharmaceutical acceptable salt thereof, and a pharmaceutical carrier or a diluent therefor.

* * * * *